United States Patent [19]
Cote et al.

[11] Patent Number: 5,209,231
[45] Date of Patent: May 11, 1993

[54] OPTICAL GLUCOSE SENSOR APPARATUS AND METHOD

[75] Inventors: Gerard L. Cote, West Willington; Martin D. Fox, Mansfield; Robert B. Northrop, Chaplin, all of Conn.

[73] Assignee: University of Connecticut, Storrs, Conn.

[21] Appl. No.: 608,251

[22] Filed: Nov. 2, 1990

[51] Int. Cl.$^5$ .............................................. A61B 5/00
[52] U.S. Cl. .................................... 128/633; 356/367; 356/368; 128/665
[58] Field of Search ............... 128/633, 634, 665, 665, 128/666; 356/364, 367, 368, 369, 41

[56] References Cited

U.S. PATENT DOCUMENTS

| | | | |
|---|---|---|---|
| 2,861,493 | 11/1958 | Landegren | 356/367 |
| 3,724,952 | 4/1973 | Vossberg | 356/366 |
| 3,958,560 | 5/1976 | March . | |
| 3,963,019 | 6/1976 | Quandt . | |
| 4,014,321 | 3/1977 | March . | |
| 4,169,676 | 10/1979 | Kaiser . | |
| 4,171,908 | 10/1979 | Robert et al. | 356/366 |
| 4,309,110 | 1/1982 | Tumerman | 356/366 |
| 4,451,149 | 5/1984 | Noeller | 356/366 |
| 4,467,204 | 8/1984 | Kysilka et al. . | |
| 4,589,776 | 5/1986 | Carver et al. | 356/367 |
| 4,629,323 | 12/1986 | Matsumoto . | |
| 4,655,225 | 4/1987 | Dahne et al. . | |
| 4,704,029 | 11/1987 | Van Heuvelen . | |
| 4,877,583 | 10/1989 | Miwa et al. . | |
| 4,882,492 | 11/1989 | Schlager . | |
| 4,889,407 | 12/1989 | Markle et al. . | |
| 4,895,159 | 1/1990 | Weiss . | |
| 4,901,728 | 2/1990 | Hutchison . | |
| 4,922,919 | 5/1990 | Novack . | |
| 4,935,346 | 6/1990 | Phillips et al. . | |
| 4,988,199 | 1/1991 | Paul | 356/368 |
| 5,068,536 | 11/1991 | Rosenthal | 128/633 |

OTHER PUBLICATIONS

"Noninvasive Glucose Monitoring of the Aqueous Humor of the Eye: Part I, Measurement of Very Small Optical Rotations", B. Rabinovitch, W. F. March and Robert L. Adams *Diabetes Care*, vol. 5, No. 3, pp. 254–258, May–Jun. 1982.

"Noninvasive Glucose Monitoring of the Aqueous Humor of the Eye: Part II. Animal Studies and the Scleral Lens" Wayne F. March, B. Rabinovitch and Robert L. Adams, *Diabetes Care*, vol. 5, No. 3, pp. 259–265, May–Jun. 1982.

"Review of Biosensors and Associated Materials Problems" W. F. Regnault and G. L. Picciolo, *J. Biomed. Mater. Res: Applied Biomaterials*, vol. 21, No. A2, pp. 163–180, 1987.

"A High-Precision Photoelectric Polarimeter", E. J. Gillham Journal of Scientific Instruments, vol. 34, pp. 434–439, Nov. 1957.

*Primary Examiner*—Lee S. Cohen
*Assistant Examiner*—Robert L. Masser, Jr.

[57] ABSTRACT

An optically based apparatus for non-invasively determining the concentration of optically active substances in a specimen comprises, a source of a beam of spatially coherent light which is acted upon to produce a rotating linear polarized vector therein. A beam splitter splits the beam into a reference beam and a detector beam for passage through the specimen. The detector beam is received upon exiting the specimen and compared with the reference beam to determine the amount of phase shift produced by passage through the specimen. This amount of phase shift is converted into concentration of the optically active substance in the specimen.

18 Claims, 3 Drawing Sheets

OPTICAL GLUCOSE SENSOR APPARATUS AND METHOD

BACKGROUND OF THE INVENTION

The present invention relates to the quantitative determination of optically active substances in specimens and, more particularly, to apparatus and methods for non-invasively determining the concentration of optically active substances.

In a number of diseases, it is desirable to monitor levels of chemical agents in the organs of patients in order to control their medication. In processes for manufacture of biogenetic materials, it is desirable to monitor chemical agents in the reactor to determine the progress of the reaction. In either instance, monitoring of the agent without invasion of the medium is desirable.

*Diabetes mellitus* is a chronic systemic disease characterized by disorders in both the metabolism of insulin, carbohydrate, fat and protein and the structure and function of blood vessels. Diabetes can result in circulatory problems which may lead to kidney failure, heart disease, gangrene and blindness. A major unanswered question in diabetes therapy is whether improved blood glucose control will alleviate the long-term complications of this disease.

Normoglycemia is difficult to achieve in diabetics because insulin injections do not adequately mimic non-diabetic insulin secretion patterns since there is no feedback control of insulin delivery rate according to the prevailing glucose level. In the last few years, there has been an intensive effort to improve metabolic control in diabetics by developing more physiological strategies of insulin administration. Three important approaches are (a) self-monitoring of blood glucose samples and adjustment of insulin dosages based on the results, (b) electromechanical devices for infusion of insulin and (c) transplantation of the pancreas or islets of Langerhans.

As is known, glucose is the main circulating carbohydrate in the body. In normal individuals, the concentration of glucose in blood is tightly regulated, usually in the range between 80 and 120 mg/100 ml, during the first hour or so following a meal. The hormone insulin, normally produced by the pancreas' beta cells, promotes glucose transport into skeletal muscle and adipose tissue as well as uptake of glucose by the liver for storage as glycogen. In *Diabetes mellitus*, insulin production and/or uptake is comprised and, consequently, blood glucose can elevate to abnormal concentrations ranging from 300 to 700 mg/100 ml. Excess insulin administration can cause severe hypoglycemia.

Although insulin deficiency can be ameliorated by treatment with diet, insulin or oral hypoglycemic agents, these standard modes of therapy have not been effective in preventing the development of chronic complications involving the eye, the kidney, the peripheral nervous system, and the peripheral arteries. Accurate determination of glucose levels in body fluids, such as blood, urine, and cerebro-spinal fluid, is a major aid in diagnosing and improving the therapeutic treatment of diabetes. It can reduce the long-term risk for developing coronary artery disease, visual impairment, renal failure, and peripheral vascular disease.

Colorimetric techniques have been developed to allow accurate self-determination of blood glucose levels by diabetic individuals. Although this method allows the patient to close the loop himself by altering the amount of insulin injected or the type and amount of food ingested, these methods are invasive and time consuming and they are especially bothersome for children. In order to overcome some of these limitations, several techniques have been proposed to continuously monitor glucose levels in the body, such as electrocatalysis.

However, there are major problems with the development of clinically useful continuous glucose sensors. In general, implanted sensors operate in the chemically and biologically harsh environment of the body for long periods of time. As such, they are subject to continuous fibrotic encapsulation and degradation which may raise questions about potential real-time responsiveness without significant delay, and the capability for integration with a pump.

Although implantation of an artificial endocrine pancreas and/or successful transplantation of islet tissue remain long range goals for improving the management of diabetes, the development of practical semi-invasive or non-invasive means for monitoring blood glucose levels could provide, if properly connected with an insulin pump through an appropriate controller, much of the potential benefit of these methods without the hazards of rejection and immunosuppression. Lastly, a noninvasive glucose sensor could have significant application in the diagnosis and management of *Diabetes mellitis* independently of the glucose pump controller applications.

An optical sensing approach using polarization rotation has been described by Rabinovitch, B., March, W. F., and Adams, R. L., in "Noninvasive Glucose Monitoring of the Aqueous Humor of the Eye; Part 1. Measurement of Very Small Optical Rotations", *Diabetes Care*, Vol. 5, No. 3; pp. 254–58, May–June 1982, and in "Noninvasive Glucose Monitoring of the Aqueous Humor of the Eye: Part II. Animal Studies and the Scleral Lens," *Diabetes Care*, Vol. 5, No. 3; pp. 259–65, May–June 1982. In their work it was found that measurement of glucose concentration in the aqueous humor of the eye correlated well with blood glucose levels with a minor time delay on the order of minutes. The glucose concentration in the aqueous humor was also found to be two orders of magnitude higher than any other optically active substances which were detected. A review of their work shows use of an amplitude measurement which is subject to a number of problems including noise susceptibility which limits the accuracy of the method.

The treatment of diabetes with prescribed injections of insulin subcutaneously results in inadequate control of glycemia compared to normal homeostatic control. Blood glucose levels rise and fall several times a day and, therefore, normoglycemia using an "open-loop" insulin delivery approach is difficult to maintain. An alternative solution to this problem would be to "close the loop" using a self-adapting insulin infusion device with a glucose biosensor which continuously detects the need for dispensing insulin at the correct rate and time.

There have been major advances in the development of reliable, versatile, and accurate insulin pumps. As mentioned, significant progress has also been made toward the development of various glucose sensors, particularly in terms of the electrocatalytic (Peura, R. A. and Mendelson, Y., "Blood Glucose Sensors: An Overview". IEEE/NSF Symposium on Biosensors: pp.

63–68, 1984; and Lewandowski, J. J., Malchesky, P. S., Zborowski, M., and Nose, Y., "Evaluation of a Miniature Blood Glucose Sensor", ASAIO Trans., 34(3); pp. 255–58, Jul.–Sep. 1988), electroenzymatic (Clark, L. C., and Noyes, L. K., "Theoretical and Practical Bases for Implantable Glucose Sensors with Special Reference to the Peritoneum", IEEE/NSF Symposium on Biosensors; pp. 69–74, 1984; Clark L. C. and Duggan, C. A., "Implanted Electroenzymatic Glucose Sensors", *Diabetes Care*, Vol. 5, No. 3, pp. 174–80, May–Jun. 1982), and various optical (Regnault, W. F., and Picciolo, G. L., "Review of Medical Biosensors and Associated Materials Problems:, *J. Biomed Mater. Res.*, Applied Biomaterials Vol. 21, No. A2; pp. 163–80, 1987, - Rabinovitch, B., March, W. F., and Adams, R. L., "Noninvasive Glucose Monitoring of the Aqueous Humor of the Eye; Part 1. Measurement of Very Small Optical Rotations", *Diabetes Care*, Vol. 5, No. 3; pp. 254–58, May–Jun. 1982; and March, W. F., Rabinovitch, B., and Adams, R. L., "Noninvasive Glucose Monitoring of the Aqueous Humor of the Eye: Part II. Animal Studies and the Scleral Lens."*Diabetes Care*, Vol. 5, No. 3, pp. 259–65, May–Jun. 1982).

However, there remain major obstacles to the development of clinically useful continuous glucose sensors. According to the National Diabetes Advisory board, in the National Long-Range Plan to Combat Diabetes, "Without a question, the most important long-term advance yet to be made is the development of a continuous blood glucose sensor." The National Institute of Diabetes, Digestive and Kidney Diseases (NIDDI) specifies that an ideal glucose sensor should include: "(a) accuracy and ability to distinguish blood glucose levels throughout the physiologic range; (b) real-time responsiveness without significant delay; (c) biocompatability and reliability for long periods: (d) small and easily implantable: (e) capability for integration with suitable pump system." (Department of Health and Human Services, Solicitation of the Public Health Service and the Health Care Financing Administration for Small Business Innovation Research (SBIR) Contract Proposals, PHS/HCFA 89-1, Due Date Dec. 9, 1988).

The principal object of the present invention is to provide a novel non-invasive optically based sensor for quantitative determination of optically active substances in a specimen.

It is also an object to provide such a sensor which exhibits a high degree of accuracy and which may be adapted for use with various types of specimens.

A specific object is to provide such a sensor which may be used for determination of glucose levels by measurement of the level in the aqueous humor.

A further object is to provide a novel and accurate non-invasive method for determination of the quantity of optically active substances in specimens.

SUMMARY OF THE INVENTION

It has now been found that the foregoing and related objects may be readily attained in an optically based apparatus for non-invasively determining concentration of optically active substances in a specimen. The apparatus includes a source of a beam of spatially coherent light, means for acting upon the light beam to produce a rotating linear polarized vector therein, and a beam splitter for splitting the beam into a reference beam and a detector beam for passage through the specimen. It also includes means for receiving the detector beam upon exiting the specimen, means comparing the reference beam with the received detector beam to determine the amount of phase shift produced by passage through the specimen, and means for converting the amount of phase shift determined into concentration of the optically active substance in the specimen.

Preferably, the means for producing the vector comprises a linear polarizer for linearly polarizing the light beam, a circular polarizer for circularly polarizing the linearly polarized beam, and a rotating linear polarizer for producing a constant amplitude time varying linear polarization in the beam. The linear polarizer polarizes the light beam to produce the field $E = E_0 a_x e^{j(\omega t - kz)}$ wherein
$E_0$ = amplitude of wave
$a_x$ = unit vector in the x direction
e = base of natural logarithm
j = square root of $-1$
$\omega$ = frequency of the light
t = time in seconds
k = wave number
z = distance in the direction of propagation The circular polarizer produces a light beam with a field, using vector notation:

$$E = \begin{pmatrix} 1 \\ j \end{pmatrix} \frac{E_o}{\sqrt{2}} e^{j(\omega t - kz)}$$

Lastly, the means for producing a rotating linear polarization vector operates at a frequency of $\omega_r/2$ to produce a field described as:

$$E = \begin{pmatrix} \cos(\omega_r t) \\ \sin(\omega_r t) \end{pmatrix} \frac{E_o}{\sqrt{2}} e^{j(\omega t - kz + \omega_r t)}$$

Generally, the reference beam is passed to a stationary linear polarizer, and there may be included a beam transport system for the detector beam from the splitter to the specimen which may include optical fibers. For optimum collimation and a limited spectrum, the light source is preferably a laser.

In a particularly useful application the specimen is the aqueous humor in the anterior chamber of the eye, which is behind the cornea and the optically active substance is glucose. To increase the path and thereby the accuracy, the apparatus desirably includes means for passing the beam through the specimen two or more times.

In the method for non-invasively sensing levels of optically active substances in a specimen, a beam of spatially coherent light is generated, a rotating linear polarized vector is produced in the light beam, after which the beam is split into a reference beam and a detector beam. The detector beam is passed through the specimen, the detector beam exiting the specimen is received and compared with the reference beam to determine the amount of phase shift produced by passage through the specimen. The amount of phase shift is then converted into a concentration value of the optically active substance in the specimen.

DETAILED DESCRIPTION OF PREFERRED EMBODIMENT OF THE INVENTION

As indicated hereinbefore, the apparatus and method of the present invention are based upon measurement of the phase shift in a polarized light beam passed through a specimen containing an optically active substance.

A principal objective of this development is the development of an optically based sensor to monitor in vivo glucose concentrations to facilitate the goal of diabetes therapy in approximating the 24 hour blood glucose profile of a normal individual. There have been major advances in the development of reliable, versatile, and accurate pumps for the delivery of insulin to diabetic patients and control algorithms for closed-loop delivery.

The polarization vector of light rotates when it interacts with an optically active material such as glucose. The amount of rotation of polarization is directly proportional to glucose concentration and to the path length. The ability to quantifify blood glucose levels with the limited available path length in the anterior chamber of the eye depends on the signal-to-noise ratio of the polarization detector and the sensitivity to measure physiologic glucose levels for the approximate one centimeter path length present in the aqueous humor of the eye.

The present invention basically utilizes a true phase technique which uses a rotating linear polarizer coupled with two stationary linear polarizers and two detectors to produce reference and signal sinusoidal outputs whose phase is equal to the rotation of light caused by the glucose solution. The sensor may also include a null point technique which uses a Faraday rotator and/or a passive contact lens for possible alignment and correction of the beam. A bidirectional technique for correction of the beam and doubling of the angle of rotation due to glucose may be used as well as optical fibers, which make it feasible to transport coherent light to and from the sensing site. The bidirectional approach couples light into both sides of the eye. The output from each side may then be compared to yield a doubled rotation angle due to glucose, and several techniques potentially may be used to reduce sensitivity to optical rotation or birefringence present in the cornea.

By inducing rotation of the linear polarization vector of the beam, it is possible to reduce the detection of change in beam polarization to a measurement of phase shift in the output beam as opposed to the measurement of amplitude variations. This method of measurement provides the opportunity for a large improvement in the signal-to-noise ratio by eliminating amplitude variations due to fluctuations in the light source or due to interaction of the optical beam with particulate matter. This may potentially eliminate the major contributor of corneal optical rotations or corneal birefringence.

Figure 1:
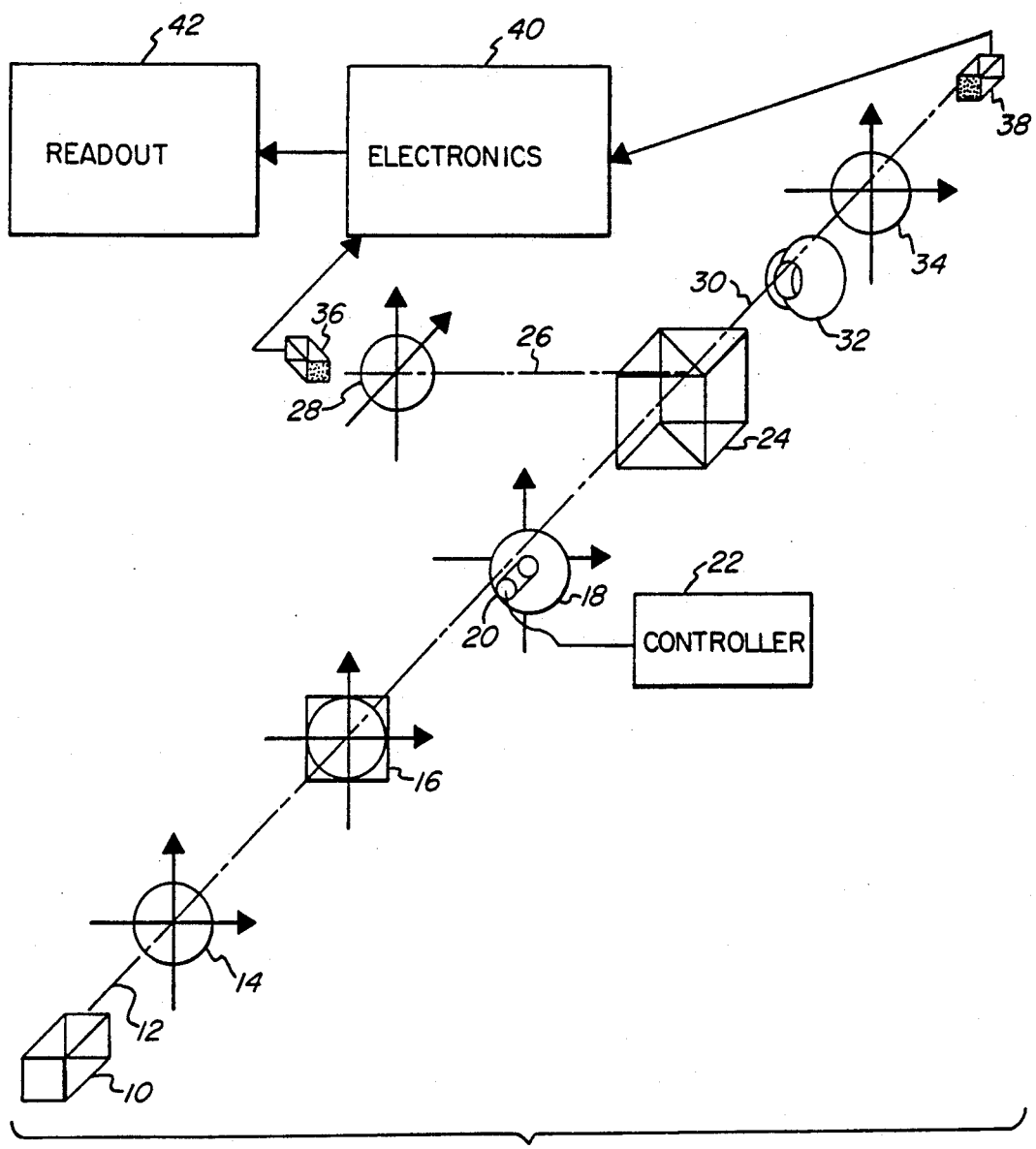
FIG. 1 is a diagrammatic illustration of non-invasive apparatus embodying the present invention for measuring glucose concentration in the aqueous humor.

Turning first to FIG. 1, therein illustrated is apparatus embodying the present invention. A coherent light source 10, currently a helium neon laser, emits a collimated beam 12. This could be a laser operating at a different frequency (i.e., infrared diode) or a coherent light source with a collimating lens. The beam 12 is then passed through a polarizing sheet 14 which linearly polarizes the light of the beam 12 to produce the following field:

$$E = E_0 a_x e^{j(\omega t - kz)}$$

The beam 12 then passes through the quarter wave plate 16 which causes the light to be circularly polarized producing the following field using vector notation:

$$E = \begin{pmatrix} 1 \\ j \end{pmatrix} \frac{E_0}{\sqrt{2}} e^{j(\omega t - kz)}$$

The circularly polarized light beam 12 is then passed through a rotating linear polarizer 18 which is affixed to a synchronous motor 20 operated by the controller 22 to rotate the polarizer at a frequency of $\omega_r/2$, thus producing a constant amplitude time varying linear polarization whose field is described as:

$$E = \begin{pmatrix} \cos(\omega_r t) \\ \sin(\omega_r t) \end{pmatrix} \frac{E_0}{\sqrt{2}} e^{j(\omega t - kz + \omega_r t)}$$

The beam 12 is then split in the beam splitter 24, and one beam 26 goes to an analyzer 28 (e.g., a stationary linear polarizer), while the other beam 30 passes through the eye 32 to a second analyzer 34. The birefringence of the cornea of the eye 32 is expressed as "$\phi$" and assumed to be along the y-axis, and the optical rotation due to glucose in the anterior chamber and any possible rotatory noise is expressed as $\theta_{sn}$. The effect the eye 32 may have on the detector beam 30 may thus be expressed in terms of the rotation and birefringence as:

$$E_{eye} = \begin{pmatrix} \cos(\omega_r t + \theta_{sn}) \\ e^{j\phi}\sin(\omega_r t + \theta_{sn}) \end{pmatrix} \frac{E_0}{2} e^{j(\omega t - kz + \omega_r t)}$$

By multiplying the above reference and signal equations by the Jones matrix for an analyzer described as:

$$M_{anal} = \begin{pmatrix} \cos^2(\theta_a) & \cos(\theta_a)\sin(\theta_a) \\ \cos(\theta_a)\sin(\theta_a) & \sin^2(\theta_a) \end{pmatrix}$$

in which the analyzers are set, with respect to the x-axis, to angles $\theta_r$ and $\theta_s$ respectively for the reference beam 26 and detector beam 30 the reference and signal beam amplitudes leaving the analyzers 28, 34 can be described as:

$$E_r = \begin{pmatrix} \cos(\theta_r)[\cos(\theta_r)\cos(\omega_r t) + \sin(\theta_r)\sin(\omega_r t)] \\ \sin(\theta_r)[\cos(\theta_r)\cos(\omega_r t) + \sin(\theta_r)\sin(\omega_r t)] \end{pmatrix} \frac{E_o}{2} e^{j(\omega t - kz + \omega_r t)}$$

$$E_s = \begin{pmatrix} \cos(\theta_s)[\cos(\theta_s)\cos(\omega_r t + \theta_{sn}) + e^{j(\phi)}\sin(\theta_s)\sin(\omega_r t + \theta_{sn})] \\ \sin(\theta_s)[\cos(\theta_s)\cos(\omega_r t + \theta_{sn}) + e^{j(\phi)}\sin(\theta_s)\sin(\omega_r t + \theta_{sn})] \end{pmatrix} \frac{E_o}{2} e^{j(\omega t - kz + \omega_r t)}$$

Each beam 26, 30 is received by its respective detector 36, 38 which picks up the intensity which is described as the electric field multiplied by its complex conjugate, i.e., $I = E_x E_x^* + E_y E_y^*$. After a series of trigonometric manipulations, the following intensities result:

$$I_r = \frac{E_o^2}{2}\{\tfrac{1}{2} + \tfrac{1}{2}\cos[2(\omega_r t - \theta_r)]\}$$

$$I_s = \frac{E_o^2}{2}\{\tfrac{1}{2} + \tfrac{1}{4}[1 - \cos(\phi)]\cos[2(\omega_r t + \theta_{sn} + \theta_s)] + \tfrac{1}{4}[1 + \cos(\phi)]\cos[2(\omega_r t + \theta_{sn} - \theta_s)]\}$$

If the analyzer angle $\theta_s$ is set to zero, or rather perpendicular to the angle of corneal birefringence, "$\phi$", the corneal birefringence term cancels out to yield a signal intensity of:

$$I_s = \frac{E_o^2}{2}\{\tfrac{1}{2} + \tfrac{1}{2}\cos[2(\omega_r t + \theta_{sn})]\}$$

If the phase shift in the detector beam 30 due to the anterior chamber of the eye 32 includes an additional term due to corneal polarization rotation (i.e., $\theta_{sn} = \theta_{ac} + \theta_n$), then this can be eliminated by the setting of the reference analyzer 36. Thus, only a phase lag due to the glucose in the anterior chamber remains.

If $\theta_n = \theta_r$, after passing these signals through the detection electronics 40 including a flip-flop which halves the frequency, the output of the phase meter of the readout 42 is equal to $\theta_{ac}$ or the phase lag due only to glucose in the anterior chamber of the eye 32. As a result, the read out 42 will provide a result indicative of the concentration of glucose in the aqueous humor.

Figure 2:
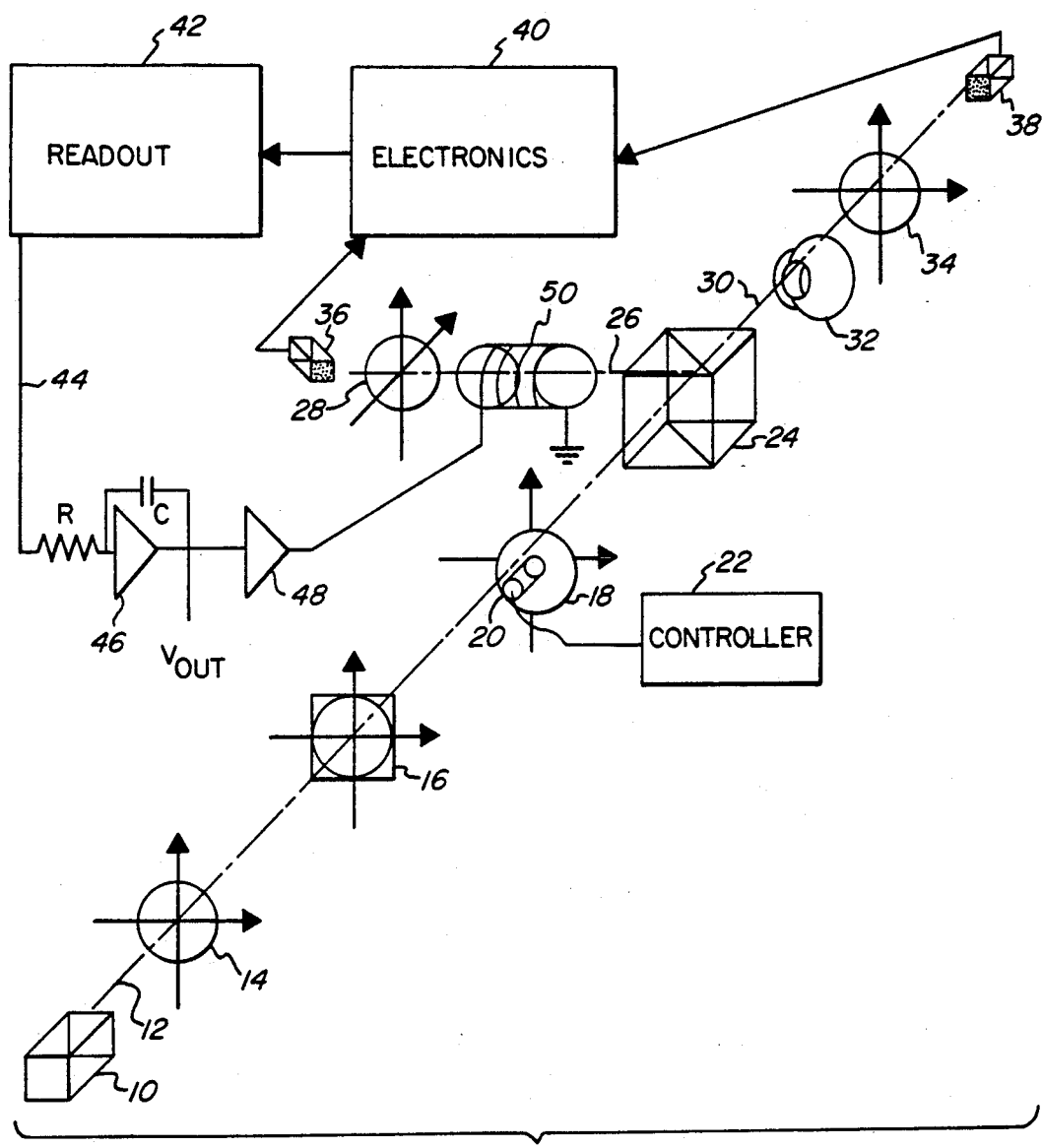
FIG. 2 is a diagrammatic illustration of another embodiment of non-invasive apparatus for the same application.

Turning now to FIG. 2, a modification of the apparatus of the present invention is illustrated wherein the output 44 of the phase meter in the readout 42 is fed back through an integrator 46 and voltage to current converter 48 to a Faraday rotary compensator 50 which rotates the polarization of the beam to compensate for the rotation in the anterior chamber, thus creating a null point method in which the voltage $V_c$ of the integrator 46 is proportional to the polarization rotation due to glucose in the eye 32.

A major problem in optical glucose detection in the eye has been corneal rotation as discussed by March and Rabinovitch B. Rabinovitch, W. F. March and R. L. Adams, "Noninvasive Glucose Monitoring of the Aqueous Humor of the Eye: Part 1. Measurement of Very Small Optical Rotations", Diabetes Care, Vol. 5, No. 3, pp. 254-65, May-June 1982; and W. F. March, B. Rabinovitch and R. L. Adams, "Noninvasive Glucose Monitoring of the Aqueous Humor of the Eye: Part II. Animal Studies and the Scleral Lens," Diabetes Care, Vol. 5, No. 3, pp. 259-65, May-June 1982.). In their report Peura et al. (R. A. Peura and Y. Mendelson, "Blood Glucose Sensors: An Overview", IEEE/NSF Symposium on Biosensors, pp. 63-68, 1984) have discussed potential problems due to corneal birefringence. If the cornea does indeed produce significant birefringence, its effects can be eliminated by the phase technique as described above. This approach should be contrasted with the technique utilized by March which applied a Faraday rotator to provide a +/−3° rotation of the incoming beam. This small rotation did not allow for a true phase detection at the output.

Figure 3:
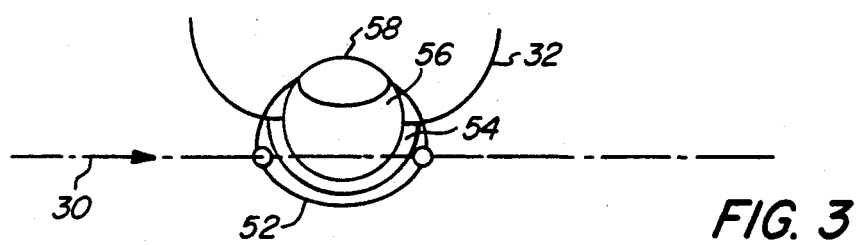
FIG. 3 is an enlarged diagrammatic illustration of an eye with the detector beam passing therethrough and including a passive contact lens.

The other potential confounding factor would be optical rotatory activity of the cornea which might be anticipated due to the presence of collagen, an optically rotatory molecule in the cornea. This effect may also be eliminated as shown above. As pointed out by March, the composition of the cornea will remain constant. Thus, the corneal rotatory contribution can be compensated either by an adjustment of the position of reference analyzer 36, or as seen in FIG. 3 by insertion of an optical element to cancel the rotation induced by the cornea 54, such as the passive contact lens 52. FIG. 3 also illustrates the anterior chamber 56 and lens 58. The contact lens 52 could also be used for alignment of the detector beam 30 in and out of the eye 32 to assure the accuracy of the path length. Further, the lens 52 could be coupled with reflective elements so as to create a multiple pass technique to increase the path length similar to that described hereinafter.

Another potential problem is that the path lengths generally available in the anterior chamber of the eye are quite short, and the amount of polarization rotation at physiologic glucose levels is generally extremely small (0.001 degrees or smaller), thus hard to detect. Because of the nature of the optical rotation if the beam were simply reflected back along the same path, this would cause the polarization rotation to unwind back to its original orientation.

Figure 4:
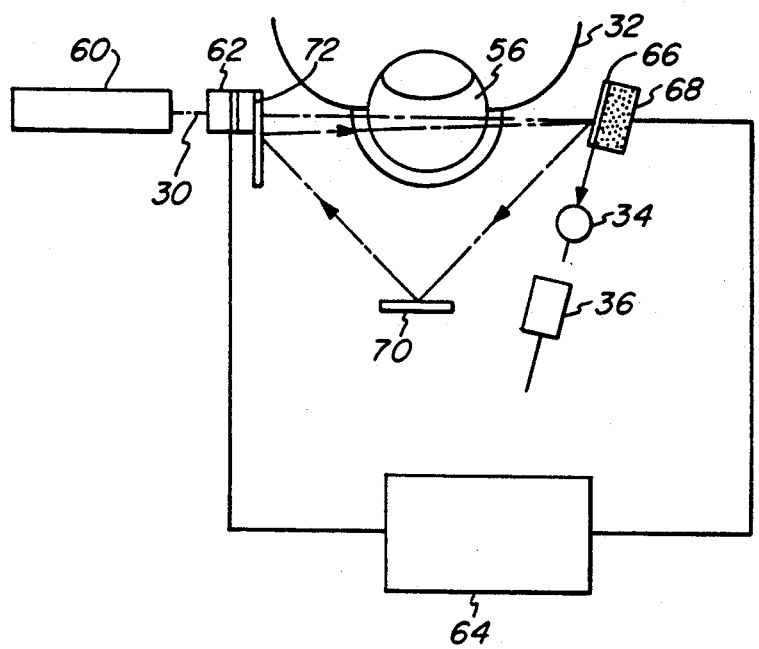
FIG. 4 is a diagrammatic illustration of one embodiment of an apparatus for providing a multiple pass of the detector beam through the eye.
Figure 5:
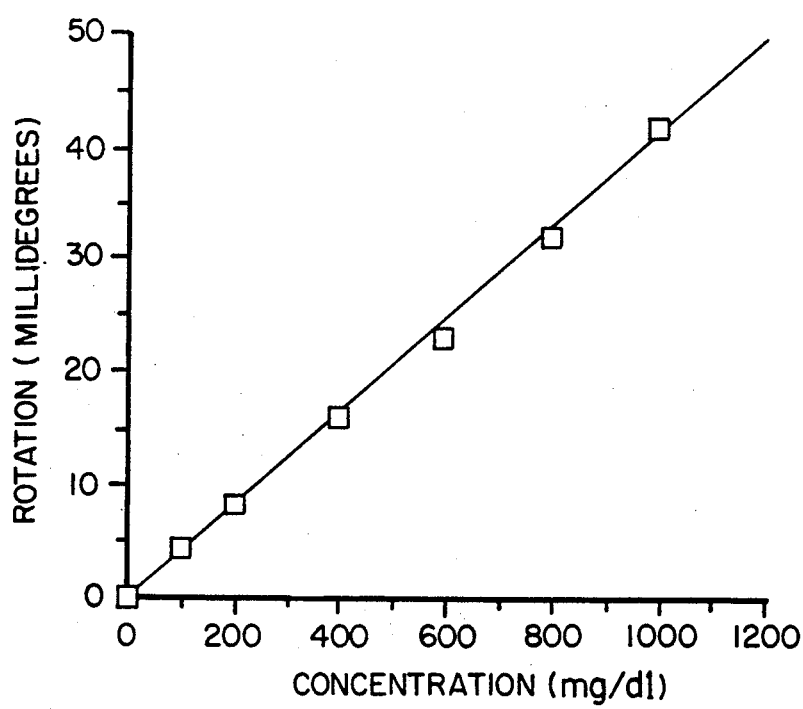
FIG. 5 is a graphic plot of observed test results and theoretical values for rotation by passage through a glucose solution.

Therefore, as seen in FIG. 4, one solution is to use a loop to direct the light back in the same direction to obtain multiple passes in the same direction through the same solution. The polarized reference beam 30 is generated from the polarizing and splitting system designated by the numeral 60 as indicated in the prior embodiments. A first shutter beam 62 is opened by the pulsed electronic control 64 to emit a nanosecond pulse of the linearly polarized light beam which passes through the anterior chamber 56 of the eye 32 and is then looped back by the mirror 66 on a piezoelectric substrate 68 and the mirror 70 to the mirror 72 through the same path for n cycles. After the length of time to complete n cycles, the first receiving mirror 66 is pivoted to direct the light beam 30 through the analyzer to the detector. If so desired, an optical amplifier, e.g., laser cavity, (not shown) could incorporate the loop to overcome any loss in intensity incurred in each pass. In place of a pivoting mirror 66, a partial mirror and shutter could be substituted.

The potential problem of proteins and other optical rotatory materials, although probably not a problem in the aqueous humor, can be confounding at other possible sensing sites. It is anticipated that specific rotation as a function of frequency would be typically different in confounding materials from that of glucose. Therefore, it may be desirable to perform the measurement at more than one optical frequency (wave length or color) and solve to eliminate the effects of the non-glucose rotatory components. It is noted that a two frequency approach was incorporated in the early work of March (supra) for determining glucose in the aqueous humor but, it is not known that it was ever tested as a discriminator, especially for other sites.

To confirm the efficiency of the apparatus and methods of the present invention, an in vitro test was performed, using the apparatus depicted in FIG. 1, using a D-glucose solution in a glass cell at physiologic glucose levels and using a 0.9 centimeter path through the solution which is comparable to path lengths anticipated in the eye. The results are graphically represented by the blocks in FIG. 4, and show good linearity and little deviation from the theoretical values which are plotted as the solid line. The maximum deviation from the linear theoretical plot for this experiment is less than 5% over the entire range studied, i.e., from 0 to 1000 mg/dl.

It will be appreciated that the apparatus as shown in the drawings can be made quite compact, and that the detector beam pathway can be arranged in a suitable probe to be placed over the eye or any other organ or specimen to be tested. The beam may also be coupled from the splitter through optical fibers which could be used to transport the beam to the sensing site.

Accordingly, the true phase sensing approach of the present invention should sense the required rotation for physiologic glucose levels at path lengths on the order of 1 cm which are present in the aqueous humor of the eye with less noise than previous amplitude sensing techniques which are sensitive to additive amplitude noise effects. This system could provide a noninvasive glucose sensor that, when combined with existing insulin infusion devices, could provide more physiologic control of blood glucose levels and it could have significant application in the diagnosis and management of diabetes mellitis independently of the glucose pump controller applications. Although the foregoing detailed description has been directed to measurement of glucose in the aqueous humor, the apparatus and method are adaptable to other applications where an optically active substance is to be measured. As one example, some biogenetic processes have optically active materials either as reactants or as products, and the apparatus and method may be used as a non-invasive tool to follow the progress of the reaction without the potential for contamination presented by sampling devices.

Thus, it can be seen from the foregoing detailed specification and claims that the apparatus and method of the present invention is one which enables non-invasive measurement of an optically active substance in vivo as well as in vitro, and the technique is free from many of the problems attendant to amplitude measurement.

Having thus described the invention, what is claimed is:

1. An optically based apparatus for in vivo non-invasively determining concentration of optically active substances in an animal comprising:

(a) a laser for producing a laser beam of spatially coherent light;
   (b) means for acting upon said laser beam to produce a rotating linear polarized vector therein including
      (i) a linear polarizer for linearly polarizing the laser beam,
      (ii) a circular polarizer for circularly polarizing the linearly polarized beam, and
      (iii) a rotating linear polarizer for producing a constant amplitude time varying linear polarization in the beam;
   (c) beam splitter means for splitting the beam into a reference beam and a detector beam for passage through a specimen;
   (d) beam transport means for transporting the detector beam to a selected area of an animal for passage through a medium in the animal containing an optically active substance;
   (e) means for receiving the detector beam upon exiting the animal;
   (f) means comparing the reference beam with the received detector beam to determine the amount of phase shift produced by rotation of the polarized light in the detector beam during passage through the animal; and
   (g) means for converting the amount of phase shift determined by said rotation of the polarized light in the detector beam into a concentration value of the optically active substance in the medium through which said detector beam has passed.

2. The optically based apparatus for non-invasively determining concentration of optically active substances in accordance with claim 1 further comprising means passing the reference beam to a stationary linear polarizer.

3. The optically based apparatus for non-invasively determining concentration of optically active substances in accordance with claim 1 wherein said beam transport means includes optical fibers.

4. The optically based apparatus for non-invasively determining concentration of optically active substances in accordance with claim 1 wherein there is included means for passing the beam through an animal at least two times to increase the path length therethrough.

5. The optically based apparatus for non-invasively determining concentration of optically active substance in accordance with claim 1 wherein there is included means for electronically modulating the light beam to null the observed phase shift resulting from elements other than the optically observed active substance in one of the light beams being compared, thereby providing a closed loop system.

6. The optically based apparatus for non-invasively determining concentration of optically active substances in accordance with claim 5 wherein the light beam which is nulled is the reference beam.

7. The optically based apparatus for non-invasively determining concentration of optically active substances in accordance with claim 5 wherein said electronic modulating means is a Faraday rotary compensator.

8. The optically based apparatus for non-invasively determining concentration of optically active substances in accordance with claim 1 wherein there is included means for nulling the observed phase shift by interposing means for electronic modification of the modality of the light beam.

9. A method for in vivo non-invasively sensing concentration of optically active substance in an animal comprising:
   (a) generating a laser beam of spatially coherent light;
   (b) producing a rotating linear polarized vector in said light beam by;
      (i) passing said light beam through a linear polarizer to linearly polarize said beam;
      (ii) passing said linearly polarized beam through a circular polarizer to circularly polarize said beam; and
      (iii) passing said circularly polarized beam through a rotating linear polarizer to produce a beam with a constant amplitude time varying linear polarization;
   (c) splitting said beam into a reference beam and a detector beam for passage;
   (d) conveying said detector beam to a selected area of an animal;
   (e) passing said detector beam through a portion of the animal having a medium containing an optically active substance to be measured;
   (f) receiving the detector beam exiting said animal;
   (g) comparing the received detector beam with said reference beam to determine the amount of phase shift produced by rotation of the polarized light in the detector beam during passage through said medium; and
   (h) converting the amount of phase shift determined by said rotation of the polarized light in the detector beam into concentration of the optically active substance in said medium through which said detector beam has passed.

10. The method of sensing concentration of an optically active substance in an animal in accordance with claim 9 including the step of passing said reference beam through a stationary linear polarizer.

11. The method of sensing concentration of an optically active substance in an animal in accordance with claim 9 wherein said method includes the step of passing said detector beam through a beam transport system from said splitter to the animal.

12. The method of sensing concentration of an optically active substance in an animal in accordance with claim 9 wherein said detector beam is passed through the aqueous humor in the anterior chamber of the eye of said animal and wherein said conversion determines the concentration of glucose as said optically active substance.

13. The method of sensing concentration of an optically active substance in an animal in accordance with claim 9 wherein said method includes the step of passing said detector beam through said animal at least two times to increase the length of its path therethrough.

14. The method of sensing concentration of an optically active substance in an animal in accordance with claim 9 wherein there is included the step of electronically modulating one of the light beams to null the observed phase shift in said one of the light beams being compared, thereby providing a closed loop system.

15. The method of sensing concentration of an optically active substance in an animal in accordance with claim 14 wherein the electronically modulating step nulls the reference beam.

16. The method of sensing concentration of an optically active substance in an animal in accordance with claim 14 wherein the step of electronic modulation is effected by use of a Faraday rotary compensator.

17. The method of sensing concentration of an optically active substance in an animal in accordance with claim 14 wherein there is included the step of nulling the observed phase shift by electronically modifying the modality of the light beam.

18. A closed loop optically based apparatus for non-invasively determining concentration of optically active substance in a specimen which eliminates light beam intensity as a variable comprising:
   (a) a laser for producing a beam of spatially coherent light;
   (b) means for acting upon said light beam to produce a rotating linear polarized vector therein;
   (c) beam splitter means for splitting the beam into a reference beam and a detector beam for passage;
   (d) means for passing said detector beam through a specimen;
   (e) means for receiving the detector beam upon exiting the specimen;
   (f) means comparing the reference beam with the received detector beam to determine the amount of phase shift produced by passage through the specimen;
   (g) means for electronically modulating the reference light beam to null the observed phase shift resulting from elements other than the optically observed active substance; and
   (h) means for converting the amount of phase shift determined into a concentration value of the optically active substance in the specimen.

* * * * *